United States Patent
Mizutani et al.

(10) Patent No.: US 6,740,769 B1
(45) Date of Patent: May 25, 2004

(54) MOLYBDENUM-BISMUTH-IRON-CONTAINING METAL OXIDE CATALYSTS FOR FLUIDIZED LAYER, METHOD FOR PREPARATION THEREOF, AND USE THEREOF

(75) Inventors: Kouichi Mizutani, Yokohama (JP); Yoshimi Nakamura, Yokohama (JP); Yutaka Sasaki, Yokohama (JP); Kunio Mori, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 10/019,292

(22) PCT Filed: Jul. 14, 2000

(86) PCT No.: PCT/JP00/04721
§ 371 (c)(1),
(2), (4) Date: Jan. 4, 2002

(87) PCT Pub. No.: WO01/05500
PCT Pub. Date: Jan. 25, 2001

(30) Foreign Application Priority Data

Jul. 21, 1999 (JP) .......................................... 11-206579

(51) Int. Cl.$^7$ ..................... C07C 253/18; C07C 253/24; B01J 31/34; B01J 21/08; B01J 23/31
(52) U.S. Cl. ..................... 558/324; 558/323; 502/110; 502/113; 502/248; 502/249; 502/255; 502/305; 502/306; 502/307; 502/308; 502/309; 502/310; 502/311; 502/312; 502/313; 502/314; 502/315; 502/316; 502/317; 502/318; 502/321; 502/322; 502/323; 502/407; 502/439
(58) Field of Search ................................. 502/110, 113, 502/248, 249, 255, 305–318, 321, 322, 323, 407, 439; 558/324, 323

(56) References Cited

U.S. PATENT DOCUMENTS

| | | | | |
|---|---|---|---|---|
| 3,226,422 A | * | 12/1965 | Sennewald et al. | 260/465.3 |
| 3,716,496 A | * | 2/1973 | Yoshino et al. | 252/439 |
| 3,816,342 A | | 6/1974 | Plank et al. | |
| 3,895,794 A | * | 7/1975 | Grasselli et al. | 260/465.3 |
| 3,988,359 A | * | 10/1976 | Saito et al. | 260/465.3 |
| 4,083,804 A | * | 4/1978 | Saito et al. | 252/432 |
| 4,107,085 A | * | 8/1978 | Sasaki et al. | 252/448 |
| 4,168,246 A | * | 9/1979 | Li | 252/437 |
| 4,246,191 A | * | 1/1981 | Pujado | 260/465.3 |
| 4,246,192 A | * | 1/1981 | Pujado | 260/465.3 |
| 4,290,922 A | * | 9/1981 | Umemura et al. | 252/456 |
| 4,370,279 A | * | 1/1983 | Sasaki et al. | 260/465.3 |
| 4,410,450 A | * | 10/1983 | Sasaki et al. | 502/22 |
| 4,587,226 A | * | 5/1986 | Sasaki et al. | 502/5 |
| 4,590,173 A | * | 5/1986 | Sasaki et al. | 502/204 |
| 4,709,070 A | * | 11/1987 | Sasaki et al. | 558/322 |
| 4,767,878 A | * | 8/1988 | Grasselli et al. | 558/324 |
| 4,774,352 A | * | 9/1988 | Sasaki et al. | 558/322 |
| 4,826,802 A | * | 5/1989 | Sasaki et al. | 502/206 |
| 4,978,765 A | * | 12/1990 | Sasaki et al. | 558/324 |
| 4,983,752 A | * | 1/1991 | Eichhorn et al. | 558/332 |
| 5,059,573 A | * | 10/1991 | Sasaki et al. | 502/205 |
| 5,071,814 A | * | 12/1991 | Sasaki et al. | 502/205 |
| 5,093,299 A | * | 3/1992 | Suresh et al. | 502/212 |
| 5,094,990 A | * | 3/1992 | Sasaki et al. | 502/214 |
| 5,132,269 A | * | 7/1992 | Sasaki et al. | 502/205 |
| 5,134,105 A | * | 7/1992 | Paparizos et al. | 502/205 |
| 5,139,988 A | * | 8/1992 | Sasaki et al. | 502/206 |
| 5,175,334 A | * | 12/1992 | Suresh et al. | 558/324 |
| 5,235,088 A | * | 8/1993 | Paparizos et al. | 558/324 |
| 5,834,394 A | * | 11/1998 | Chen et al. | 502/302 |
| 5,877,381 A | * | 3/1999 | Sasaki et al. | 585/658 |
| 6,057,471 A | * | 5/2000 | Nakamura et al. | 558/321 |
| 6,187,943 B1 | * | 2/2001 | Sasaki et al. | 558/318 |

FOREIGN PATENT DOCUMENTS

| | | |
|---|---|---|
| EP | 43684 | 1/1982 |
| EP | 0 383 598 A1 * | 8/1990 |
| EP | 0 389 255 A1 * | 9/1990 |
| EP | 0 484 792 A1 * | 5/1992 |
| EP | 0 750 942 | 1/1997 |
| JP | 57-65329 | 4/1982 |
| JP | 2-214543 | 8/1990 |
| JP | 8-141401 | 4/1996 |
| WO | WO 99/54037 | 10/1999 |

* cited by examiner

*Primary Examiner*—Cam N. Nguyen
(74) *Attorney, Agent, or Firm*—Oblon, Spivak, McClelland, Maier & Neustadt, P.C.

(57) ABSTRACT

A process for producing a molybdenum-bismuth-iron-containing metal oxide fluidized bed catalyst which has a controlled particle diameter and has satisfactory activity and physical properties. In a process for producing a fluidized bed catalyst containing molybdenum-bismuth-iron and silica as a carrier component, dried products formed in a spray drying step and having a particle diameter outside a desired range are pulverized, then the pulverized one is mixed into a slurry before spray drying, the resulting mixture is spray-dried, and the spray-dried particles are subjected to a classification operation to obtain particles having a diameter within the desired range, which are then calcined. The catalyst produced according to the present invention is suitable for producing acrylonitrile by ammoxidation of propylene.

17 Claims, No Drawings

MOLYBDENUM-BISMUTH-IRON-CONTAINING METAL OXIDE CATALYSTS FOR FLUIDIZED LAYER, METHOD FOR PREPARATION THEREOF, AND USE THEREOF

TECHNICAL FIELD

The present invention relates to a process for producing a molybdenum-bismuth-iron-containing metal oxide fluidized bed catalyst. In more particular, it relates to a process for producing a particle diameter-controlled molybdenum-bismuth-iron-containing metal oxide fluidized bed catalyst having a desired particle diameter distribution.

Further, the present invention relates to a molybdenum-bismuth-iron-containing metal oxide fluidized bed catalyst obtained by the above-mentioned process, the use of the catalyst, and a process for producing acrylonitrile or methacrylonitrile which uses the catalyst.

BACKGROUND ART

The use of a molybdenum-bismuth-containing metal oxide fluidized bed catalyst in ammoxidation of propylene, isobutene and/or tertiary butanol is disclosed, for example, in JP-B-36-3563, JP-B-36-5870, JP-B-38-17967, JP-B-39-3670, JP-B-39-10111, JP-B-42-7774, JP-B-50-64191, JP-B-47-27490, JP-B-54-22795 and JP-B-60-36812.

With regard to a process for producing a fluidized bed catalyst having a controlled particle diameter distribution, proposals have been made in JP-A-52-140490 as to an iron-antimony type oxide fluidized bed catalyst and in JP-A-5-261301 as to a vanadium-phosphorus type oxide fluidized bed catalyst. However, no effective method has been proposed as to a process for producing a molybdenum-bismuth-iron-containing metal oxide fluidized bed catalyst.

DISCLOSURE OF THE INVENTION

It is well known that, in a fluidized bed reaction, in order to keep catalyst particles in a good fluidizing condition thereby to make the reaction proceed efficiently, it is very important that the physical property, particularly the particle diameter distribution, of the catalyst is appropriate.

In producing a fluidized bed catalyst, it is usually conducted for obtaining a catalyst having a desired particle diameter distribution to control the conditions of spray drying. By such a means alone, however, it is quite difficult to produce the intended catalyst, and catalyst particles having unnecessarily large or small diameters tend to be inevitably formed. When the amount of catalyst particles having small diameters is too large, in a fluidized bed reaction, such catalyst particles tend to fly away during the reaction to cause an increase in the amount of the catalyst to be replenished. In particular, catalyst particles with a diameter of 20 $\mu$m or less are apt to fly out of the system. When the amount of catalyst particles having a large diameter is too large, the fluidizing property of the catalyst tends to deteriorate to worsen the result of the reaction.

Furthermore, even when a catalyst having an appropriate particle diameter distribution is used in a fluidized bed reaction, the catalyst particles with small diameters gradually fly away during the reaction to shift the particle diameters toward larger ones. In such a case, measure is commonly taken in which a catalyst containing much of fine particles is replenished so that the catalyst in the reactor may keep an appropriate particle diameter distribution. In preparing the catalyst used for replenishing mentioned above, it is difficult to obtain a catalyst of the desired particle diameter distribution by mere control of the spray drying conditions. Therefore, it is economically advantageous to use a supplementary catalyst having controlled particle diameters produced by the combination of the control of spray drying conditions with the removal by classification of particles with a diameter of 20 $\mu$m or less, which are apt to fly away. Further, it is favorable if the fine particles removed by classification can be reused as the catalyst starting material.

However, no such methods have been disclosed with regard to a molybdenum-bismuth-iron-containing metal oxide fluidized bed catalyst. Moreover, even when such a known method is applied as such to the present catalyst system, satisfactory results cannot be obtained because the activity and physical property of the catalyst are adversely affected. It is estimated that, in a catalyst of the present system, when the catalyst particles removed by classification and having particle diameters outside the desired range are added to a slurry before spray drying, the solution composition-precipitation composition ratio becomes different from that in the initial catalyst slurry, which may exert a great influence on the performance characteristics of the catalyst. Under such situations, development of a process has been awaited which can produce a molybdenum-bismuth-iron-containing metal oxide fluidized bed catalyst having controlled particle diameters economically efficiently while keeping good catalytic characteristics.

After extensive study, the present inventors have found that, in a process for producing a metal oxide fluidized bed catalyst containing molybdenum, bismuth, iron and silica as the essential constituents of the catalyst component, by separating dried particulate products with particle diameters outside the desired particle diameter range from spherical particles obtained by spray drying operation, pulverizing the dried products to particle diameters of 10 $\mu$m or less, then mixing the pulverized products into the slurry at a stage prior to spray drying within the range of 50% by weight or less (based on the oxides of the completed catalyst), spray-drying the resulting mixture, and subjecting the spray-dried product to classificatio, catalyst particles having diameters outside the desired particle diameter range can be effectively utilized and, as a whole, a practically useful molybdenum-bismuth-containing metal oxide fluidized bed catalyst which has a high strength, particularly excellent abrasion resistance, and moreover sufficient activity can be produced in a reasonable way.

Thus, according to the present invention, there is provided a process for producing a molybdenum-bismuth-iron-containing metal oxide fluidized bed catalyst containing molybdenum, bismuth, iron and silica as essential components and having a controlled particle diameter, said process comprising the step of spray-drying a slurry containing catalyst components to effect granulation, which comprises the steps of

[I] spray-drying a slurry containing catalyst components,

[II] subjecting the dry particles obtained by the spray drying to classification to separate dry particles having a particle diameter outside a desired range, and feeding dry particles having a particle diameter within the desired range to the subsequent calcination step,

[III] pulverizing the dry particles having a particle diameter outside the desired range so as to have a particle diameter of 10 $\mu$m or less to obtain a pulverized product, and

[IV] mixing the pulverized product into the slurry containing catalyst components at any desired stage prior to the spray drying so as to be in the range of not more than 50% by weight in terms of oxides based on oxides of a completed catalyst obtained after the spray drying and the calcination.

The metal oxide fluidized bed catalyst produced by the process for producing a metal oxide fluidized bed catalyst of the present invention described above is preferably a catalyst having a composition represented by the formula $$Mo_a Bi_b Fe_c Q_d R_e X_f Y_g O_h (SiO_2)_i$$

wherein Mo, Bi, Fe and O respectively represent molybdenum, bismuth, iron and oxygen, Q represents at least one element selected from the group consisting of nickel, cobalt, magnesium, chromium, manganese and zinc, R represents at least one element selected from the group consisting of beryllium, phosphorus, boron, arsenic, selenium, lithium, sodium, potassium, rubidium, cesium, thallium and tellurium, X represents at least one element selected from the group consisting of vanadium, tungsten, yttrium, lanthanum, zirconium, hafnium, niobium, tantalum, aluminum, calcium, strontium, barium, lead, copper, cadmium, gallium, indium, germanium, antimony, tin and cerium, Y represents at least one element selected from the group consisting of praseodymium, neodymium, samarium, europium, gadolinium, thorium, uranium, rhenium, ruthenium, rhodium, palladium, osmium, iridium, platinum, silver and gold, and $SiO_2$ represents silica; suffixes a, b, c, d, e, f, g, h and i represent atomic ratios of the respective elements, provided that when a=10, then $0.1 \leq b \leq 5$, $0.1 \leq c \leq 10$, $0 \leq d \leq 8$, $0 \leq e \leq 3$, $0 \leq f \leq 8$, $0 \leq g \leq 2$ and $10 \leq i \leq 200$; and h is the number of oxygen atoms necessary for satisfying valencies of the above respective components.

Further, according to the present invention, there are provided a molybdenum-bismuth-iron-containing metal oxide fluidized bed catalyst obtained by the above-mentioned process, a process for using the catalyst, and a process for producing acrylonitrile or methacrylonitrile which uses the catalyst.

BEST MODE FOR CARRYING OUT THE INVENTION

The catalyst itself having the composition represented by the formula mentioned above may be produced by any desired method, but it is particularly preferable that the respective components be closely mixed together to form one body.

The starting materials of the respective component elements for producing the catalyst may be selected from oxides or from chlorides, sulfates, nitrates, ammonium salts, carbonates, hydroxides, organic acid salts, oxyacids, oxyacid salts, heteropolyacids, heteropolyacid salts, and the mixtures thereof which can be converted into oxides by ignition. The ratios of the amounts of these materials to be used may be appropriately varied according to the composition ratios of respective elements in the final catalyst obtained.

The materials for the molybdenum component which may be used are, for example, oxides such as molybdenum trioxide; molybdic acid or its salts, such as molybdic acid, ammonium paramolybdate and ammonium metamolybdate; and heteropolyacids containing molybdenum, such as phosphomolybdic acid and silicomolybdic acid, or their salts. Preferably used is ammonium paramolybdate or ammonium metamolybdate.

The materials for the bismuth component which may be used are, for example, bismuth salts, such as bismuth nitrate, bismuth carbonate, bismuth sulfate and bismuth acetate; bismuth trioxide and metallic bismuth. These material may be used as a solid as it is, or as aqueous solution or aqueous nitric acid solution, or as a slurry of bismuth compound formed from these aqueous solutions, but it is preferable to use a nitrate, or its solution, or a slurry formed from the solution.

The materials for the iron component which may be used are, for example, ferrous oxide, ferric oxide, ferrous nitrate, ferric nitrate, iron sulfate, iron chloride, organic acid iron salts and iron hydroxide and, further, a solution obtained by dissolving metallic iron in heated nitric acid. Solutions containing an iron component may be used after pH-controlled with aqueous ammonia or the like. Preferably, ferrous nitrate or ferric nitrate is used.

As for the material for the silica component, it is convenient to use a suitable silica sol selected from those available on the market.

As for the other materials, preferably used are oxides, or nitrates, carbonates, organic acid salts, hydroxides, etc., or the mixtures thereof which can be converted into oxides by ignition; more preferably used are nitrates.

A slurry containing the catalyst components can be prepared by closely mixing the above-mentioned catalyst raw materials so as to give a desired composition. The preparation of the slurry may be done by any known methods, for example, the methods described in JP-B-37-8568, JP-B-57-49253, JP-B-54-12913, JP-B-51-1674, JP-A-2-59046, and JP-A-2-214543. The means for mixing the raw materials in the slurry preparation and the conditions of slurry preparation, such as temperature, pressure and atmosphere, may be set as desired.

The respective catalyst components may be mixed in successive order, in the form of solid or solution, into silica sol or water. It is also possible to conduct pH control and/or heat treatment in the course of the slurry preparation step. The solutions of the respective catalyst components used for the slurry preparation may be one obtained by dissolving partial, plural components beforehand or one which has been further subjected to pH control and heat treatment. These operations exert no particular effect on the effect of the present invention.

In controlling the pH, the iron component can be prevented from precipitating by making a chelating agent coexist in the solution containing the iron component. The chelating agent which may be used is, for example, ethylenediaminetetraacetic acid, lactic acid, citric acid, tartaric acid and gluconic acid. In making an aqueous solution containing an iron ion and a chelating agent, it is preferable to dissolve these raw materials in acid or water.

The slurry thus prepared is then subjected to spray drying, whereby substantially spherical particles are formed. The spray drying conditions are not particularly limited. Spray driers of pressure nozzle type, two fluid nozzle type and rotating disk type, etc. may be used for the spray drying. The concentration of the slurry subjected to spray drying is preferably about 10–50% by weight in terms of the oxides of elements constituting the catalyst.

The spray drying temperature also is not particularly limited but, when the temperature is extremely high, care must be taken because in addition to the general tendency of the shape of the catalyst becoming worse, in some cases in the application of the present example, the spray-dried product tends to be difficulty pulverized. For example, the spray drying can be conducted at a temperatures in the range of 100–500° C., or in the range of 150–350° C. The pressure and the atmosphere in the spray drying may be set as desired.

From the spherical particles formed by the spray drying are separated extra fine particles and/or coarse particles which are not suited to practical use. Cakes which form at the time of spray drying (owing to the deposit or the like on the inner wall of the spray drying apparatus) may also be regarded as coarse particles. The particle diameters of the extra fine particles and/or the coarse particles to be separated vary depending on the intended reactors and reaction conditions and also on the particle density of the catalyst. Therefore, it is preferable to determine the particle diameters to be separated by taking the properties and the using conditions of the catalyst into consideration. The conditions of the separation, for example, means for separation, temperature, pressure and atmosphere in the separation may be set as desired.

The range of diameters of the particles to be separated is preferably not more than 10–20 μm for extra fine particles and not less than 100–300 μm for coarse particles. In particular, for extra fine particles, it is preferable to separate particles of 20 μm or less and, for coarse particles, it is preferable to separate those of 200 μm or more, more preferably those of 150 μm or more. The term "particle diameter" herein refers not to the average particle diameter of the whole particles but to the particle diameter of individual particles.

When the separation is necessary, separately a classifier may be used. Known classifiers, e.g., sieves, cyclones and pneumatic classifiers, may be used. However, particularly when the production of the above-mentioned replenishing catalyst is intended, a catalyst is desired which has a narrow particle diameter distribution on the relatively small particle diameter side and contains neither extra fine particles nor coarse particles, so that the efficiency of particle diameter control at this time is quite important.

Separated particles with particle diameters outside the desired range are, according to necessity, pulverized by using a known grinding machine (pulverizer), such as a colloid mill, ball mill and vibrating mill. The grinding conditions, such as grinding means, temperature, pressure and atmosphere, may be set as desired. The method of wet grinding is particularly preferable. At this time, the particles may be mixed with water, or mixed with a catalyst starting material or with a slurry before spray drying. Though the particles which have undergone the spray drying step have a strength sufficient for the above-mentioned particle diameter controlling operation conducted, for example, by classification, they can be relatively easily pulverized and, according to the wet grinding method, most of the particles can be pulverized to 10 μm or less in a short time.

When large particles get mingled in the slurry, the shape of the resulting completed catalyst tends to be poor. Therefore, it is preferable to pulverize most of the particles to 10 μm or less, more preferably 5 μm or less. More specifically, pulverization is preferably conducted until the proportion of particles of 10 μm or less, preferably 5 μm or less, reaches 50% by weight or more, preferably 80% by weight or more, particularly preferably 95% by weight or more. Since particles which have undergone a calcination step have a high strength and require much energy for pulverization, particle diameter control is preferably applied to spray-dried particles.

The pulverized particles thus obtained are mixed into the above-mentioned slurry before spray drying and used. The mixing conditions, e.g. mixing means, temperature, pressure and atmosphere, may be set as desired. The mixing may be done at any stages before spray drying, for example, the stage of catalyst raw material mixing, the stage of pH controlling, and before or after the stage of heat treatment. Though the mixing can be conducted in any stage, it is preferable to mix the particles into the slurry immediately before the spray drying from the viewpoints of the rationality and the reproducibility of operation.

The amount of the spray-dried, pulverized product to be mixed is preferably not more than 50% by weight, more preferably in the range of 1–50% by weight, still more preferably in the range of 2–30% by weight, in terms of oxides based on the oxides of the completed catalyst. When the pulverized product is mixed in an amount exceeding 50% by weight, the resulting ratio of solution composition to precipitation composition in the slurry differs greatly from that in the initial catalyst slurry, so that the reaction characteristics of the catalyst tend to be poor. When the mixing proportion of the catalyst particles removed by classification is 1% or less, it tends to be difficult to obtain a fluidized bed catalyst having particle diameters controlled to the desired range.

The slurry containing pulverized particles prepared as described above is then formed into substantially spherical particles by being subjected to spray drying.

The spray-dried product containing substantially no extra fine particles and/or coarse particles obtained by separating extra fine particles and/or coarse particles is then calcined to give a catalyst. The calcination conditions, e.g., calcining means, temperature, pressure and atmosphere, may be set as desired. Such a spray-dried product is calcined to give a catalyst by heat treatment in the temperature range of preferably 200° C.–800° C., more preferably 400° C.–750° C. for, e.g., 0.5–10 hours. The gas atmosphere used in the calcination may be either an oxidizing gas atmosphere containing oxygen or an inert gas atmosphere, e.g., nitrogen, but air is conveniently used. The calcination may be conducted by using, for example, a box type furnace, tunnel furnace, rotary furnace and fluidization furnace.

Though the above-mentioned metal oxide fluidized bed catalyst in the present invention is not particularly restricted so long as it has the composition represented by the above-mentioned formula, preferably the Q element is at least one element selected from the group consisting of nickel, cobalt, magnesium, chromium and manganese, the R element is at least one element selected from the group consisting of potassium, phosphorus, sodium, rubidium, cesium and tellurium, the X element is at least one element selected from the group consisting of cerium, vanadium, tungsten, lanthanum, zirconium, niobium, tantalum, aluminium, gallium, germanium, antimony and tin, and the Y element is at least one element selected from the group consisting of praseodymium, neodymium, samarium, rhenium, ruthenium, rhodium, palladium, iridium and platinum.

In the above-mentioned formula (1), preferable atomic ratios of the respective elements are, when a=10, then $0.2 \leq b \leq 4$, $0.2 \leq c \leq 8$, $0 \leq d \leq 7.5$, $0 \leq e \leq 2$, $0 \leq f \leq 7.5$, $0 \leq g \leq 1.5$ and $20 \leq i \leq 150$.

The catalyst produced as described above is filled in a fluidized bed reactor, and an olefin of a starting material, oxygen, ammonia, etc. are fed into the reactor, whereby an ammoxidation reaction can be effected. The starting olefin is preferably propylene or isobutene. The oxygen source preferably used is air on account of economical advantage, but air appropriately enriched with oxygen may also be used. If necessary and desired, an inert gas, such as nitrogen or steam, may also be fed to the reactor. In this way, acrylonitrile or methacrylonitrile can be obtained.

PREFERRED EMBODIMENTS OF THE INVENTION

The present invention is described in detail below with reference to Examples and Comparative Examples, but the invention is in no way limited thereto. The composition ratios of the respective elements in the catalyst obtained were calculated from the amounts of the raw materials of the respective constituent elements on the assumption that the total amounts of the respective constituent elements (Mo, Bi, Fe, Q component, R component, X component, Y component and $SiO_2$) contained in the starting materials used for catalyst preparation are incorporated as such into the catalyst.

The process of the present invention is described further in detail with reference to Examples.

The activity test of the catalysts in Examples and Comparative Examples was conducted as follows. The catalyst used for the test was one from which coarse particles (including broken cake pieces) of 200 μm or more had been separated by classification in order to obtain a good fluidizing condition during the reaction. The catalyst was filled in a reactor having a built-in cyclone in which the inner diameter of the catalyst fluidizing part is 2 inches, so that a predetermined contact period of time might be attained. A reaction starting material gas comprising propylene, ammonia and air in a molar ratio of 1:1.2:10 was charged into the reactor to give a linear velocity of 15 cm/sec. The reaction temperature was 440° C. and the reaction pressure was 200 kPa. The reaction products were quantitatively analyzed by gas chromatography. The propylene conversion and acrylonitrile yield in the activity test of the catalyst prepared in Examples and Comparative Examples are defined as follows.

Propylene conversion (%)=(number of moles of reacted propylene)/(number of moles of fed propylene)×100

Acrylonitrile yield (%)=(number of moles of acrylonitrile formed)/(number of moles of fed propylene)×100

The strength of the catalyst prepared in Examples and Comparative Examples was determined in the following manner.

The strength test was made by using the method of determination of the collapse (crushing) strength of catalyst particles according to the description of JP-A-9-70542. The "collapse strength" herein refers to the pressure at which the particles collapse (crush) when an increasingly higher pressure is applied to the particles. The values of collapse strength shown in Table 1 are those determined by using a Shimadzu MCTM-200 (a trade mark, mfd. by Shimadzu Corp.) under the following measuring conditions.

indenter: upper indenter (indenting tool):
  made of diamond, 500 μm plane indenter;
lower indenter: made of SUS
loading rate: 0.72 gram-weight/sec
sample: catalyst of particles having particle diameters of 45–50 μm The sample particles having particle diameters of 45–50 μm were obtained by sieving with a Micro Mesh Precision Sieves (a trade mark, mfd. by Buckee Mears. Co. St. Paul). The average of values determined for 30 points randomly selected from the above-mentioned particles having diameters of 45–50 μm was taken as the collapse strength of the sample. Examples 1 and 2

An oxide composition of which the empirical formula is represented by $Mo_{10}Bi_{0.8}Fe_{1.7}Ni_{2.1}Co_{3.75}Mn_{0.8}$—$Cr_{0.4}K_{0.08}O_{41.84}(SiO_2)_{40}$ was prepared in the following manner.

In 4,000 g of pure water was dissolved 3,689 g of ammonium paramolybdate with heating, and then 25,110 g of 20% silica sol was added thereto while stirring. To the resulting solution was added a solution of 1,276 g of nickel nitrate, 2,281 g of cobalt nitrate, 335 g of chromium nitrate, 959 g of 50% manganese nitrate and 17 g of potassium nitrate dissolved in 2,500 g of pure water, and the resulting mixture was stirred. Thereto was then added with stirring a solution of 811 g of bismuth nitrate, 1,435 g of ferric nitrate and 300 g of citric acid dissolved in 1,000 g of 10% nitric acid. The pH of the resulting slurry was adjusted with 15% aqueous ammonia finally to 8 and the slurry was heat-treated at 100° C. for 1 hour. The slurry of this stage thus prepared is hereinafter referred to as "completed slurry". Thereafter the slurry was spray-dried with a rotary disc spray drier while controlling the inlet temperature at 320° C. and the outlet temperature at 160° C. At this time, by regulating the cyclone, extra fine particles with diameters of 20 μm or less were separated by classification. The extra fine particles thus separated were subjected to wet grinding with a ball mill so that 99% or more of the ground particles might have diameters of 10 μm or less. The ground particles thus obtained were added to a completed slurry prepared in the same manner as described above so that the added amount might be 20% by weight (Example 1) or 50% by weight (Example 2) in terms of oxides in the completed (final) catalyst after firing (calcination). Thereafter, each of the resultant slurries was spray-dried in the same manner as described above, and extra fine particles with diameters of 20 μm or less were separated by classification. The particles thus obtained from which extra fine particles had been separated and removed were heat-treated at 250° C., then fired (calcined) at 400° C. for 2.5 hours and finally fired at 600° C. for 3 hours.

COMPARATIVE EXAMPLE 1

A catalyst was prepared in the same manner as in Examples 1 and 2 except that the classification-separation of extra fine particles by regulating the cyclone at the time of spray drying was not conducted, thus particles of all particle diameters were collected and the recycle use of separated particles was not conducted. The proportion of particles with diameters of 20 μm or less (indicated as −20 μm in the table) in the completed catalyst was 15% by weight.

COMPARATIVE EXAMPLE 2

A catalyst was prepared in the same manner as in Examples 1 and 2 except that the product obtained by wet grinding of extra fine particles with a ball mill was added to the completed catalyst so as to be 70% by weight in terms of oxides of the completed catalyst.

EXAMPLES 3 AND 4

An oxide composition of which the empirical formula as represented by $Mo_{10}Bi_{0.28}Fe_{1.8}Mg_{2.1}Mi_{3.4}$—$Ce_{0.84}K_{0.17}O_{39.965}$ $(SiO_2)_{35}$ was prepared in the following manner.

To 2,000 g of pure water was added 837 g of 61% nitric acid, and then 256 g of bismuth nitrate, 688 g of cerium nitrate, 1,371 g of ferric nitrate, 1,865 g of nickel nitrate, 1,015 g of magnesium nitrate and 32.4 g of potassium nitrate were added thereto and stirred. The resulting mixture was designated "A liquid". A solution obtained by dissolving with heating 3,329 g of ammonium paramolybdate in 7,000 g of pure water was designated "B liquid". To 19,830 g of 20% silica sol were added the A solution and the B solution in said order with stirring to obtain a completed slurry. The completed slurry was spray-dried, during which extra fine particles of 20 μm or less were classification-separated by regulation of the cyclone. The separated extra fine particles were subjected to wet grinding with a ball mill so that 99% or more of the ground particles might have diameters of 10 μm or less. The ground particles thus obtained were added to a completed slurry prepared in the same manner as described above so that the added amount might be 10% by weight (Example 3) or 40% by weight (Example 4) in terms of oxides of the completed catalyst after firing. Thereafter, each of the resultant slurries was spray-dried in the same manner as described above, and extra fine particles with diameters of 20 μm or less were separated by classification. The particles thus obtained containing no extra fine particles were heat-treated at 250° C., then fired at 400° C. for 2.5 hours and finally fired at 640° C. for 3 hours.

COMPARATIVE EXAMPLE 3

A catalyst was prepared in the same manner as in Examples 3 and 4 except that the classification-separation of extra fine particles by regulating the cyclone at the time of spray drying was not conducted, thus particles of all particle diameters were collected and the recycle use of separated particles was not conducted. The proportion of particles with diameters of 20 μm or less in the completed catalyst was 18% by weight.

COMPARATIVE EXAMPLE 4

A catalyst was prepared in the same manner as in Examples 3 and 4 except that the product obtained by wet grinding of extra fine particles with a ball mill was added to the completed slurry so as to be 60% by weight in terms of the oxides of the completed catalyst.

EXAMPLES 5 AND 6

An oxide composition of which the empirical formula is represented by $Mo_{10}Bi_{0.4}Fe_{1.3}Ni_6Cr_{0.4}Ce_{0.4}$—$K_{0.2}O_{40.45}$ $(SiO_2)_{35}$ was prepared in the following manner.

In 30,000 g of pure water was dissolved 3,465 g of ammonium paramolybdate, and then mixed thereinto a solution of 381 g of bismuth nitrate, 40 g of potassium nitrate, 3,425 g of nickel nitrate, 314 g of chromium nitrate, 341 g of cerium nitrate and 250 g citric acid dissolved in 2,700 g of 3.3% nitric acid. To the resulting mixture were added a solution prepared by dissolving 1,031 g of ferric nitrate and 250 g of citric acid in 2,700 g of pure water, and then 20,640 g of 20% silica sol. While the resulting slurry was being stirred, 15% aqueous ammonia was added thereto to adjust the pH to 2. The slurry was then heat-treated at 98° C. for 1.5 hours to obtain a completed slurry. The completed slurry was spray-dried, during which extra fine particles of 20 μm or less were classification-separated by regulation of the cyclone. Coarse particles of 200 μm or more formed in the spray drying were also separated by classification. These particles and the cake formed at the time of spray drying were subjected to wet grinding with a ball mill so that 99% or more of the ground particles might have diameters of 10 μm or less. The ground particles thus obtained were added to a completed slurry prepared in the same manner as described above so that the added amount might be 10% (Example 5) or 30% (Example 6) in terms of the oxides of the completed catalyst. Thereafter, each of the resultant slurries was spray-dried in the same manner as described above, and extra fine particles of 20 μm or less were separated by classification. The particles thus obtained containing no extra fine particles were heat-treated at 250° C., then fired at 400° C. for 2.5 hours and finally fired at 660° C. for 3 hours.

COMPARATIVE EXAMPLE 5

A catalyst was prepared in the same manner as in Examples 5 and 6 except that the classification-separation of extra fine particles by regulating the cyclone at the time of spray drying was not conducted, thus particles of all particle diameters were collected and the recycle use of classified particles was not conducted. The proportion of particles with diameters of 20 μm or less (indicated as −20 μm in the table) in the completed catalyst was 14% by weight.

COMPARATIVE EXAMPLE 6

A catalyst was prepared in the same manner as in Examples 5 and 6 except that the product obtained by wet-grinding extra fine particles, coarse particles and the cake formed at the time of spray drying with a ball mill was added to the completed slurry so as to be 60% by weight in terms the oxides of the completed catalyst.

Table 1 shows the results of catalyst strength tests, the results of activity tests and the particle diameter distributions of the catalysts of Examples and Comparative Examples.

TABLE 1

| | Test Results | | | | | | |
|---|---|---|---|---|---|---|---|
| | Ground product concentration (wt %) | Collapse strength (g) | Contact time (s) | Reaction time elapse (hr) | Propylene conversion (%) | Acrylonitrile yield (%) | Particle diameter distribution −20 μm (wt %) |
| Example 1 | 20 | 16 | 4.5 | 3 | 95.5 | 76.6 | 1 |
| | | | | 50 | 95.3 | 76.5 | 1 |
| Example 2 | 50 | 13 | 4.5 | 3 | 96.2 | 76.4 | 2 |
| Comparative Example 1 | 0 | 16 | 4.5 | 3 | 95.0 | 76.9 | 15 |
| | | | | 50 | 93.4 | 75.6 | 9 |
| Comparative Example 2 | 70 | 8 | 4.5 | 3 | 96.4 | 73.2 | 1 |
| Example 3 | 10 | 12 | 4.5 | 3 | 98.3 | 79.4 | 0 |
| | | | | 50 | 98.4 | 79.3 | 0 |
| Example 4 | 40 | 10 | 4.5 | 3 | 97.8 | 79.0 | 0 |
| Comparative Example 3 | 0 | 12 | 4.5 | 3 | 97.5 | 79.1 | 18 |
| | | | | 50 | 96.6 | 77.5 | 5 |

TABLE 1-continued

Test Results

|  | Ground product concentration (wt %) | Collapse strength (g) | Contact time (s) | Reaction time elapse (hr) | Propylene conversion (%) | Acrylonitrile yield (%) | Particle diameter distribution −20 μm (wt %) |
|---|---|---|---|---|---|---|---|
| Comparative Example 4 | 60 | 6 | 4.5 | 3 | 98.0 | 77.8 | 1 |
| Example 5 | 10 | 10 | 4.5 | 3 | 97.5 | 80.1 | 1 |
|  |  |  |  | 50 | 97.2 | 79.8 | 1 |
| Example 6 | 30 | 11 | 4.5 | 3 | 97.8 | 79.8 | 0 |
| Comparative Example 5 | 0 | 10 | 4.5 | 3 | 97.9 | 80.0 | 14 |
|  |  |  |  | 50 | 96.1 | 78.3 | 5 |
| Comparative Example 6 | 60 | 8 | 4.5 | 3 | 98.0 | 78.3 | 1 |

Table 1 reveals that the catalysts of Examples have both a good activity and a good physical property. On the other hand, the catalysts of Comparative Examples 2, 4 and 6, which contain a large amount of ground spray-dried products show a decreased acrylonitrile yield and a decreased collapse strength. Furthermore, in the case of the catalysts of Comparative Examples 1, 3 and 5, from which extra fine particles have not been separated by classification, extra fine particles with diameters of 20 μm or less gradually fly away during the reaction and the acrylonitrile yield decreases as the reaction time lengthens from 3 hours to 50 hours.

INDUSTRIAL APPLICABILITY

According to the process of the present invention, extra fine particles and coarse particles separated from spherical particles obtained by spray drying of a slurry can be reused without wastage, and hence the catalyst production yield can be improved. Further, since the above-mentioned particles are spray-dried products, they can be easily ground and, in spray-drying a slurry containing the above-mentioned ground particles, spherical particles can be produced without causing the problem of abrasing the apparatus. Moreover, the catalyst having controlled particle diameters thus produced is a practically useful one which has a high strength and sufficient activity.

Moreover, the completed catalyst has a low content of extra fine particles and hence the loss of catalyst during the reaction is small, and the unit requirement of catalyst is improved. Correspondingly, the amount of waste catalyst formed decreases markedly, which is favorable for operation. Furthermore, without causing an adverse phenomenon wherein part of the fine particles fly away during reaction to shift the particle diameter distribution toward larger one and resultantly to deteriorate the fluidizing state and lower the acrylonitrile yield and propylene conversion, a catalyst having particle diameters in the desired range alone, that is, a catalyst having a desired particle diameter distribution and containing substantially neither extra fine particles nor coarse particles, can be produced. By replenishing such a catalyst into the reaction system, the improvement of fluidizing state and the improvement of acrylonitrile yield and propylene conversion can be achieved. Though an optimum particle diameter distribution may vary also according to the scale and type of the reactor, it has become possible to meet a wide range of requirements by application of the process of the present invention.

What is claimed is:

1. A process for producing a molybdenum-bismuth-iron-containing metal oxide fluidized bed catalyst containing molybdenum, bismuth, iron and silica as essential components and having a controlled particle diameter, the process comprising:

spray-drying a slurry containing catalyst components to effect granulation, subjecting the dry particles obtained by the spray-drying to classification to separate dry particles having a particle diameter outside a desired range, and feeding dry particles having a particle diameter within the desired range to subsequent calcination step, pulverizing the dry particles having a particle diameter outside the desired range so as to have a particle diameter of 10 μm or less to obtain a pulverized product, and mixing the pulverized product into the slurry containing catalyst components at any desired stage prior to the spray-drying so as to be in the range of not more than 50% by weight in terms of oxides based on oxides of a completed catalyst after the spray drying and the calcination, wherein the metal oxide fluidized bed catalyst is a catalyst having a composition represented by the formula

where

Mo, Bi, Fe and O respectively represent molybdenum, bismuth, iron and oxygen,

Q represents at least one element selected from the group consisting of nickel, cobalt, magnesium, chromium, manganese and zinc.

R represents at least one element selected from the group consisting of beryllium, phosphorus, boron, arsenic, selenium, lithium, sodium, potassium, rubidium, cesium, thallium and tellurium, X represents at least one element selected from the group consisting of vanadium, tungsten, yttrium, lanthanum, zirconium, hafnium, niobium, tantalum, aluminum, calcium, strontium, barium, lead, copper, cadmium, gallium, indium, germanium, antimony, tin and cerium, Y represents at least one element selected from the group consisting of praseodymium, neodymium, samarium, europium, gadolinium, thorium, uranium, rhenium, ruthenium, rhodium, palladium, osmium, iridium, platinum, silver and gold, and $SiO_2$ represents silica;

suffixes a, b, c, d, e, f, g, h and i represent atomic ratios of the respective elements. provided that when a=10, then $0.1 \leq b \leq 5$, $0.1 \leq c \leq 10$, $0 \leq d \leq 8$, $0 \leq e \leq 3$, $0 \leq f \leq 8$, $0 \leq g \leq 2$ and $10 \leq i \leq 200$; and h is the number of oxygen atoms necessary for satisfying valencies of the above respective components.

2. The process for producing the metal oxide fluidized bed catalyst according to claim 1, wherein the process comprises, in the step, mixing the pulverized product so as to be in the range of 1–50% by weight in terms of oxides based on the oxides of the completed catalyst.

3. The process for producing the metal oxide fluidized bed catalyst according to claim 2, wherein the process comprises mixing the pulverized product so as to be 2–30% by weight in terms of oxides based on the oxides of the completed catalyst.

4. The process for producing the metal oxide fluidized bed catalyst according to claim 1, wherein the metal oxide fluidized bed catalyst is used for producing acrylonitrile or methacrylonitrile by ammoxidation of propylene or isobutene.

5. The process for producing the metal oxide fluidized bed catalyst according to claim 4, wherein the metal oxide fluidized bed catalyst is used for producing acrylonitrile by ammoxidation of propylene.

6. The process for producing the metal oxide fluidized bed catalyst according to claim 1, wherein the process further includes the step of preparing the slurry containing the catalyst components and the step of calcining the dry particles having a particle diameter within the desired range to obtain the metal oxide fluidized bed catalyst.

7. The process for producing the metal oxide fluidized bed catalyst according to claim 6, wherein the step of preparing the slurry comprises controlling pH, and said pH control is achieved by making at least one chelating agent selected from the group consisting of ethylenediaminetetraacetic acid, lactic acid, citric acid, tartaric acid and gluconic acid coexist in a solution containing an iron component to prevent a precipitation of the iron component.

8. The process for producing the metal oxide fluidized bed catalyst according to claim 6, wherein the calcination is conducted at a temperature of 200–800° C.

9. The process for producing the metal oxide fluidized bed catalyst according to claim 8, wherein the calcination is conducted at a temperature of 400–750° C.

10. The process for producing the metal oxide fluidized bed catalyst according to claim 1, wherein the Q element is at least one element selected from the group consisting of nickel, cobalt, magnesium, chromium and manganese, the R element is at least one element selected from the group consisting of potassium, phosphorus, sodium, rubidium, cesium and tellurium, the X element is at least one element selected from the group consisting of cerium, vanadium, tungsten, lanthanum, zirconium, niobium, tantalum, aluminum, gallium, germanium, antimony and tin, and the Y element is at least one element selected from the group consisting of praseodymium, neodymium, samarium, rhenium, ruthenium, rhodium, palladium, iridium and platinum; and the atomic ratios of the respective elements in the above-mentioned formula are: when a=10, then $0.2 \leq b \leq 4$, $0.2 \leq c \leq 8$, $0 \leq d \leq 7.5$, $0 \leq e \leq 2$, $0 \leq f \leq 7.5$, $0 \leq g \leq 1.5$ and $20 \leq i \leq 150$.

11. The process for producing the metal oxide fluidized bed catalyst according to claim 1, wherein the process comprises, in the step, separating fine particles having a particle diameter of 20 μm or less and coarse particles having a particle diameter of 100 μm or more.

12. The process for producing the metal oxide fluidized bed catalyst according to claim 1, wherein the process comprises, in the step, pulverizing the dry particles so as to have a particle diameter of 5 μm or less.

13. A molybdenum-bismuth-iron-containing metal oxide fluidized bed catalyst containing molybdenum, bismuth, iron and silica as essential components and having a controlled particle diameter produced by the process according to claim 1.

14. A process for conducting an ammoxidation reaction of olefin using the metal oxide fluidized bed catalyst of claim 13.

15. The process according to claim 14 wherein the ammoxidation reaction is conducted by using propylene or isobutene as the olefin in the presence of oxygen and ammonia.

16. A process for producing acrylonitrile or methacrylonitrile comprising contacting raw materials with the metal oxide fluidized bed catalyst of claim 13.

17. The process according to claim 16, wherein the raw materials comprise oxygen, ammonia and an olefin selected from the group consisting of propylene and isobutene.

* * * * *